United States Patent [19]

Aoki et al.

[11] Patent Number: 4,600,541

[45] Date of Patent: Jul. 15, 1986

[54] PROCESS FOR THE PREPARATION OF ACRYLONITRILE OR METHACRYLONITRILE

[75] Inventors: Kunitoshi Aoki, Kawasaki; Shigeo Nakamura, Yokohama, both of Japan

[73] Assignee: Asahi Kasei Kogyo Kabushiki Kaisha, Osaka, Japan

[21] Appl. No.: 794,323

[22] Filed: Nov. 1, 1985

Related U.S. Application Data

[63] Continuation of Ser. No. 603,537, Apr. 25, 1984, abandoned.

[30] Foreign Application Priority Data

May 6, 1983 [JP] Japan .................................. 58-78290

[51] Int. Cl.$^4$ .................................. C07C 120/14
[52] U.S. Cl. .................................. 558/321; 502/209; 502/212; 502/205; 502/242; 502/243; 502/245; 502/248; 502/249
[58] Field of Search .................................. 260/465.3

[56] References Cited

U.S. PATENT DOCUMENTS

| | | | |
|---|---|---|---|
| 2,904,530 | 9/1959 | Idol, Jr. | 260/465.3 |
| 3,156,735 | 11/1964 | Armstrong | 260/465.3 X |
| 3,347,900 | 10/1967 | Gossel et al. | 260/465.3 |
| 3,407,223 | 10/1968 | Kominami et al. | 260/465.3 |
| 3,412,136 | 11/1968 | McClain et al. | 260/465.3 |
| 3,415,886 | 12/1968 | McClellan | 260/465.3 UX |
| 3,470,230 | 9/1969 | Hirsch et al. | 260/465.3 |
| 3,499,025 | 3/1970 | Thomas | 260/465.3 |
| 3,553,246 | 1/1971 | Kominami et al. | 260/465.3 |
| 3,625,867 | 12/1971 | Yoshino et al. | 260/465.3 X |
| 3,766,092 | 10/1973 | Honda et al. | 260/465.3 X |
| 3,911,089 | 10/1975 | Shiraishi et al. | 260/465.3 X |
| 4,139,552 | 2/1979 | Grasselli et al. | 260/465.3 |
| 4,228,098 | 10/1980 | Aoki et al. | 260/465.3 |
| 4,443,556 | 4/1984 | Aoki et al. | 260/465.3 X |

FOREIGN PATENT DOCUMENTS 1243175 6/1967 Fed. Rep. of Germany .

*Primary Examiner*—Joseph Paul Brust
*Attorney, Agent, or Firm*—Sprung Horn Kramer & Woods

[57] ABSTRACT

In the preparation of acrylonitrile or methacrylonitrile by ammoxidation of propylene or isobutylene with ammonia and molecular oxygen in the vapor phase in the presence of a catalyst comprising silica and supported thereon oxides of molybdenum, bismuth and iron, the yield of acrylonitrile or methacrylonitrile based on ammonia is improved without sacrificing the yield based on propylene or isobutylene by the use of a novel catalyst having, incorporated therein, 0.002 to 0.2 atom, based on 12 atoms of molybdenum, of an oxide of at least one element selected from the group consisting of palladium, platinum, osmium and iridium.

16 Claims, 1 Drawing Figure

FIGURE
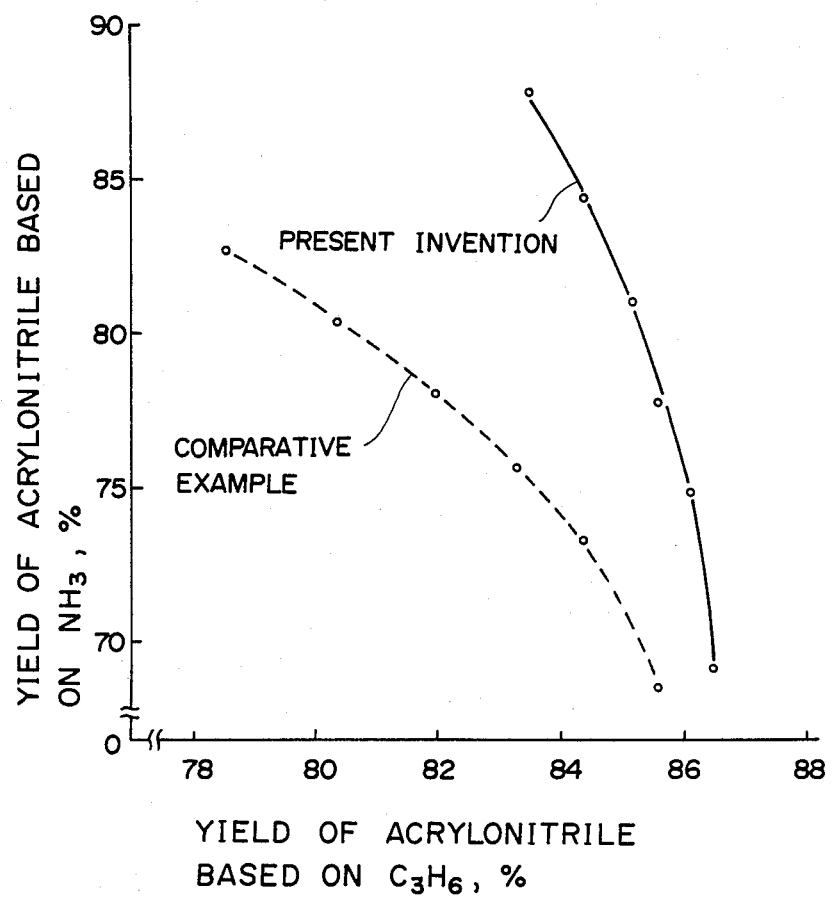

PROCESS FOR THE PREPARATION OF ACRYLONITRILE OR METHACRYLONITRILE

This application is a continuation of application Ser. No. 603,537, filed Apr. 25, 1984, now abandoned.

This invention relates to a process for the preparation of acrylonitrile or methacrylonitrile by the ammoxidation of propylene or isobutylene. More particularly, the present invention is concerned with a process for the preparation of acrylonitrile or methacrylonitrile by the vapor phase reaction of propylene or isobutylene with ammonia and molecular oxygen in the presence of an improved catalyst containing oxides of molybdenum, bismuth, iron and a specific ingredient in specific proportion.

The process of producing acrylonitrile or methacrylonitrile by the vapor phase oxidation of propylene or isobutylene with molecular oxygen in the presence of ammonia is well known as the "ammoxidation of propylene or isobutylene," and widely practiced on a large scale. As the catalysts to be used in the ammoxidation reaction of propylene or isobutylene, there have been proposed many kinds of catalysts (see for example, U.S. Pat. No. 2,904,580, German Pat. No. 1,243,175, U.S. Pat. Nos. 4,228,098, 3,766,092, and 4,139,552). These proposed catalysts, however, have disadvantages, particularly that a so-called "ammonia efficiency" is low. That is, conventionally, when the catalysts are used in the ammoxidation of propylene or isobutylene, the yield of the desired acrylonitrile or methacrylonitrile based on propylene or isobutylene is high but that based on ammonia is relatively low.

As is well known, nowadays due to the increase in the price of hydrogen which is a raw material of ammonia, the price of ammonia has been remarkably increased. For this reason, the yield of acrylonitrile or methacrylonitrile based on ammonia has a great effect on the price of acrylonitrile or methacrylonitrile. In this respect, the conventional catalysts which are relatively poor in the yields of acrylonitrile and methacrylonitrile based on ammonia are not satisfactory from the commercial point of view. In view of the fact as mentioned above, these days acrylonitrile and methacrylonitrile is produced on a large scale, even a few percent increase in yield of acrylonitrile and metharylonitrile based on ammonia leads to an extremely large economical advantage.

The present inventors have made extensive and intensive studies with a view to developing a catalyst for the ammoxidation of propylene or isobutylene which can increase the yield of acrylonitrile or methacrylonitrile based on ammonia (hereinafter often referred to as "ammonia-based yield") without sacrificing the yield of acrylonitrile or methacrylonitrile based on propylene or isobutylene (hereinafter often referred to as "olefin-based yield"). As a result, the present inventors have found that when a minute amount of oxide of at least one element selected from palladium, platinum, osmium and iridium is incorporated as a further ingredient into a catalyst containing oxides of molybdenum, bismuth and iron, the ammonia-based yield is remarkably increased without sacrificing the olefin-based yield. The present invention has been made based on such a novel finding.

Accordingly, it is an object of the present invention to provide a process for the preparation of acrylonitrile or methacrylonitrile by the ammoxidation of propylene or isobutylene in the presence of a catalyst, which can produce the desired acrylonitrile or methacrylonitrile not only in high olefin-based yield but also in high ammonia-based yield.

The foregoing and other objects, features and advantages of the present invention will be apparent to those skilled in the art from the following detailed description taken in connection with the accompanying drawing in which:

FIGURE is a graph showing the relationship between the yield of acrylonitrile based on propylene and that based on ammonia, with respect to the catalyst to be used in the process of the present invention, shown in comparison with that of the conventional catalyst.

According to the present invention, there is provided a process for the preparation of acrylonitrile or methacrylonitrile comprising contacting propylene or isobutylene with ammonia and molecular oxygen in the vapor phase in the presence of an oxide catalyst comprising silica and supported thereon a composition containing oxides of molybdenum, bismuth, iron and an ingredient A, said ingredient A being at least one element selected from the group consisting of palladium, platinum, osmium and iridium and being present in an amount of 0.002 to 0.2 atom based on 12 atoms of molybdenum.

In the process of the present invention, the oxide catalyst (hereinafter often referred to simply as "catalyst") to be used comprises silica and supported thereon a composition containing oxides of molybdenum, bismuth, iron and an ingredient A. The ingredient A is at least one element selected from the group consisting of palladium, platinum, osmium and iridium. Of the above elements, palladium is preferable. The amount of the ingredient A is 0.002 to 0.2 atom, preferably 0.005 to 0.1 atom based on 12 atoms of molybdenum. Where the amount of the ingredient A is less than 0.002 atom based on 12 atoms of molybdenum, no significant increase in ammonia-based yield can be attained. On the other hand, where the amount of the ingredient A is larger than 0.2 atom based on 12 atoms of molybdenum, the formation of carbon dioxide is unfavorably increased. With respect to the amount of bismuth and iron, it is preferred that bismuth and iron each be present in an amount of 0.5 to 10, preferably 1 to 8 based on 12 atoms of molybdenum.

In addition to the oxides of molybdenum, bismuth, iron and the ingredient A, the catalyst to be employed in the present invention may contain, as an optional ingredient, an oxide of at least one member selected from the group consisting of alkali metals, alkaline earth metals (metals of Group IIA of the Periodic Table), rare earth elements (having an atomic number of from 57 to 71), Sn, Pb, Ti, Zr, W, V, Nb, Cr, Mn, Co, Ni, Zn, Cu, In, Tl, B and Sb. The atomic ratio of the above-mentioned member, based on 12 atoms of molybdenum, may be generally 10 or less, preferably 5 or less. When at least one member selected from the group consisting of potassium, rubidium and cesium, out of alkali metals, is employed as the optional ingredient, it is preferred that the atomic ratio thereof, based on 12 atoms of molybdenum, be 0.5 or less. Of the alkaline earth metals, Be, Mg, Ca, Sr and Ba are preferred.

The catalyst to be employed in the present invention may further contain phosphorus. The atomic ratio of phosphorus, based on 12 atoms of molybdenum, may be in the range of from 0.1 to 3. The phosphorus ingredient does not have any substantial effect on the activity and selectivity of the catalyst. However, the generally-recognized addition effect of phosphorus, which means that addition of phosphorus is effective in stabilizing a slurry of catalyst raw materials and improving the abrasion resistance of the catalyst obtained therefrom, is recognized with respect to the oxide catalyst to be employed in the present invention as well.

In the catalyst to be used in the present invention, a composition containing the above-mentioned essential ingredients and the optional ingredients is supported on silica. Silica may be employed in an amount of generally from 30 to 70% by weight, preferably 40 to 60% by weight, based on the catalyst. Where the silica content is less than 30% by weight, the catalyst has a decreased abrasion resistance. On the other hand, where the silica content is greater than 70% by weight, the catalyst exhibits a low activity, i.e. a low conversion of propylene or isobutylene.

As the source of a support silica, a silica sol may be suitably employed. As the source of phosphorus, there may preferably be employed aqueous phosphoric acid. As the source of each metal to be incorporated in the present catalysts, there may advantageously be employed respective salts, for example, ammonium salts, nitrates, chlorides, sulfates and salts of organic acids such as oxalic acid, acetic acid and the like. Particularly, in respect of the source of molybdenum, it is preferable to employ an ammonium salt of molybdenum, and in respect of the sources of bismuth and iron, there are preferably employed nitrates thereof.

The catalyst to be employed in the present invention may be prepared according to any of the customary methods (see, for example, column 2, line 72 to column 3, line 25 of U.S. Pat. No. 2,904,580). For example, the catalyst may be prepared by first adding under agitation to a silica sol an aqueous solution, or aqueous nitric acid solution, of metal salts. to obtain a slurry, then evaporation-drying or spray-drying the slurry to obtain a dried product and finally calcining the dried product at a temperature of from 550° to 750° C., preferably from 600° to 710° C. Further, the catalyst may also be suitably prepared by first producing a precursor catalyst, in which the ingredient A is not contained, in accordance with the above-described method, then impregnating the precursor catalyst with a solution of the ingredient A to obtain an impregnated product and finally calcining the impregnated product at a temperature of from 350° to 750° C., preferably from 400° to 710° C. In preparing the catalyst to be used in the present invention, the calcination time may vary depending on calcination temperature and the kind of catalysts to be prepared, but is generally 1 to 24 hours.

Production of acrylonitrile or methacrylonitrile according to the present invention may be performed either in a fluidized bed reactor or in a fixed bed reactor. The reactants, i.e., propylene, isobutylene and ammonia are not necessarily required to be of high purity, but of industrial grade. In place of isobutylene, tert-butanol, which is converted to isobutylene in the reactor, may be used. The source of oxygen is not critical. However, air may be advantageously utilized. In the process of the present invention, various diluent gases, such as steam, nitrogen gas and carbon dioxide gas, may be employed to dilute a mixture of propylene or isobutylene, ammonia and oxygen in such an amount that the intended reaction is not adversely affected.

The volume ratio of oxygen to propylene or isobutylene is preferably in the range of from 1.7 to 2.7. The volume ratio of ammonia to propylene or isobutylene may vary in a wide range. However, it is especially preferred that the volume ratio of ammonia to propylene be in the range of from 0.95 to 1.15, and that the volume ratio of ammonia to isobutylene be in the range of from 1.15 to 1.35. When each of the above-mentioned volume ratios of ammonia is smaller than the respective lower limit of the range, the product yield based on propylene or isobutylene disadvantageously drops. On the other hand, when it is greater than the respective upper limit of the range, the product yield based on ammonia is disadvantageously decreased. The reaction temperature may be in the range of generally from 400° to 500° C., preferably from 410° to 480° C. The ammoxidation reaction may be conducted under an atmospheric pressure. According to need, however, it may be conducted under a super-atmospheric pressure, ususally not exceeding about 2 Kg/cm$^2$-gauge. The time of contact of mixed gaseous raw materials with the catalyst may be in the range of generally from 0.2 to 10 seconds, preferably from 0.4 to 6 seconds.

As described in the foregoing, the process for the preparation of acrylonitrile or methacrylonitrile according to the present invention is characterized by using an oxide type catalyst which contains, as active ingredient, molybdenum, bismuth and iron and a specific amount of at least one element selected from the group consisting of palladium, platinum, osmium and iridium. By the use of such a specific catalyst, acrylonitrile or methacrylonitrile can be produced not only in high olefin-based yield but also in high ammonia-based yield.

The present invention will now be illustrated in more detail by the following Examples that should not be construed as limiting the scope of the invention.

REFERENCE EXAMPLE

Preparation of Catalysts

A catalyst composed of oxides supported on 50% by weight, based on the total of the oxides and silica, of silica and having a composition, in terms of active ingredients, of the formula: $Pd_{0.02} Mo_{12} Bi_{4.1} Fe_{7.2} K_{0.07} P_{1.0}$ was prepared according to the following procedures.

1.73 g of an 85% by weight aqueous solution of phosphoric acid were added to 166.7 g of "Snowtex N"(trade name of a silica sol manufactured by Nissan Kagaku Kabushiki Kaisha, Japan; "Snowtex" is a registered trade mark) containing 30% by weight of $SiO_2$, while stirring the same, followed by addition of an aqueous solution of 32.07 g of ammonium heptamolybdate tetrahydrate $[(NH_4)_6Mo_7O_{24}.4H_2O)]$ dissolved in 80 g of water. To the resulting mixture was added a solution composed of 29.83 g of bismuth nitrate pentahydrate $[Bi(NO_3)_3.5H_2O]$, 43.93 g of ferric nitrate nonahydrate $[Fe(NO_3)_3.9H_2O]$ and 0.070 g of palladium nitrate $[Pd(NO_3)_2]$ dissolved in 33 g of a 13% by weight aqueous solution of nitric acid to obtain a slurry. Subsequently, the raw material slurry thus obtained was dried at about 200° C. by means of a parallel flow type spray drier. The raw material slurry was atomized by means of a centrifugal type spraying apparatus equipped with a dish type rotor and disposed in the center of the upper part of the spray drier. The dried powder thus obtained was transferred to a tunnel type calcining kiln in which the powder was sujected to pre-calcination at 400° C. for one hour, followed by calcination at 690° C. for 2 hours to obtain a catalyst. The catalyst thus obtained will be referred to as "Catalyst 6-A" hereinafter.

Substantially the same procedures as described above were repeated except that the use of $Pd(NO_3)_2$ as the metal source was omitted. As a result, there was obtained a catalyst of which the composition was same as that of Catalyst 6-A except that Pd was not contained. 20 g of the so obtained catalyst was charged into a beaker, followed by addition of 3 ml of an aqueous solution of 0.014 g of palladium nitrate [Pd(NO$_3$)$_2$], thereby to cause the catalyst to be impregnated with the palladium nitrate solution. The resultant was calcinated at 500° C. for 2 hours to obtain Catalyst 6-B.

Further, catalysts having various compositions were prepared in substantially the same manner as in preparation of Catalyst 6-A except that the kind and amount of the metal sources and the calcination temperature were varied. The composition of each of the so prepared catalysts was determined by calculation based on the amounts of the metal sources employed. The compositions thus determined by the calculation are shown in Table 1.

With respect to the ingredients of each catalyst indicated in Table 1, the following compounds were used as the metal sources: H$_2$PtCl$_6$.6H$_2$O, IrCl$_4$, OsCl$_3$, Ca(NO$_3$)$_2$.4H$_2$O, Ce(NO$_3$)$_3$.6H$_2$O, Ni(NO$_3$)$_2$.6H$_2$O, Sb$_2$O$_3$, Pb(NO$_3$)$_2$, TiO$_2$, (NH$_4$)$_{10}$H$_{10}$W$_{12}$O$_{46}$.6H$_2$O, Mn(NO$_3$)$_2$.6H$_2$O, Zn(NO$_3$)$_2$.6H$_2$O, Cu(NO$_3$)$_2$.3H$_2$O, TlNO$_3$, Mg(NO$_3$)$_2$.6H$_2$O, Co(NO$_3$)$_2$.6H$_2$O, CsNO$_3$, RbNO$_3$, ZrO(NO$_3$)$_2$.2H$_2$O, NH$_4$VO$_3$, SnCl$_2$.2H$_2$O, Nb$_2$O$_5$, Cr(NO$_3$)$_3$.9H$_2$O, In(NO$_3$)$_3$.3H$_2$O, H$_3$BO$_3$, NaNO$_3$, AgNO$_3$, Sr(NO$_3$)$_2$, La(NO$_3$)$_3$.6H$_2$O and Sm(NO$_3$)$_3$.6H$_2$O.

In the meantime, the amount of each ingredient present in each catalyst obtained above was examined by the following method:

(1) The amount of the ingredient A

Examination was made according to the atomic absorption method, using an atomic absorption spectrometer Model AA-620 manufactured and sold by Shimadzu Corporation, Japan.

(2) Other ingredients than the ingredient A

Examination was made according to the wet analysis or according to the X-ray fluorometry using a fluorescent X-ray analyzer GEIGERFLEX D-9C manufactured and sold by Rigaku Corporation, Japan.

As a result, it was confirmed that the composition of each catalyst determined by the above examination was equal to that shown in Table 1, i.e., that obtained by the calculation.

TABLE 1

| Catalyst | Composition of Catalyst | | | | | | SiO$_2$ (% by weight) | Calcination temperature (°C.) |
|---|---|---|---|---|---|---|---|---|
| | A | Mo | Bi | Fe | P | Others | | |
| 1* | — | 12 | 4.1 | 7.2 | 1 | — | 50 | 700 |
| 2 | Pd 0.02 | " | " | " | " | — | " | " |
| 3* | — | " | " | " | " | K 0.07 | " | 690 |
| 4 | Pd 0.006 | " | " | " | " | " | " | " |
| 5 | Pd 0.01 | " | " | " | " | " | " | " |
| 6-A | Pd 0.02 | " | " | " | " | " | " | " |
| 6-B | " | " | " | " | " | " | " | 690→500 |
| 7 | Pd 0.05 | " | " | " | " | " | " | 690 |
| 8 | Pt 0.003 | " | " | " | " | " | " | " |
| 9 | Pt 0.01 | " | " | " | " | " | " | " |
| 10 | Os 0.03 | " | " | " | " | " | " | " |
| 11 | Ir 0.03 | " | " | " | " | " | " | " |
| 12 | ( Pd 0.01 / Pt 0.003 ) | " | " | " | " | " | " | " |
| 13 | ( Pd 0.01 / Os 0.005 ) | " | " | " | " | " | " | " |
| 14 | ( Pt 0.01 / Ir 0.005 ) | " | " | " | " | " | " | " |
| 15* | — | " | 3.4 | 6.6 | " | ( K 0.07 / Ca 0.4 ) | " | " |
| 16 | Pd 0.02 | " | " | " | " | ( K 0.07 / Ca 0.4 ) | " | " |
| 17* | — | " | 3.0 | 6.8 | 0.3 | ( K 0.07 / Ce 0.4 ) | " | 700 |
| 18 | Pd 0.02 | " | " | " | " | ( K 0.07 / Ce 0.4 ) | " | " |
| 19* | — | " | 3.1 | 4.8 | 1 | ( K 0.07 / Ni 4 ) | " | 670 |
| 20 | Pd 0.02 | " | " | " | " | ( K 0.07 / Ni 4 ) | " | " |
| 21* | — | " | 4.1 | 7.2 | " | ( K 0.07 / Sb 0.5 ) | " | 690 |
| 22 | Pd 0.02 | " | " | " | " | ( K 0.07 / Sb 0.5 ) | " | " |
| 23 | " | " | " | " | " | Rb 0.04 | " | 680 |
| 24 | " | " | " | " | " | Cs 0.03 | " | " |
| 25 | " | " | " | " | " | ( K 0.07 / Sn 1 / K 0.07 ) | " | 690 |

TABLE 1-continued

| Catalyst | Composition of Catalyst | | | | | | $SiO_2$ (% by weight) | Calcination temperature (°C.) |
|---|---|---|---|---|---|---|---|---|
| | A | Mo | Bi | Fe | P | Others | | |
| 26 | " | " | " | " | " | Ti 0.2 | " | " |
| 27 | " | " | " | " | " | K 0.07, Zr 0.5 | " | " |
| 28 | " | " | " | " | " | K 0.07, W 1 | " | " |
| 29 | " | " | " | " | " | K 0.07, V 0.1 | " | " |
| 30 | " | " | " | " | " | K 0.07, Nb 0.5 | " | " |
| 31 | " | " | " | " | " | K 0.07, Cr 0.1 | " | " |
| 32 | " | " | " | " | " | K 0.07, Mn 0.5 | " | 680 |
| 33 | " | " | " | " | " | K 0.07, Zn 0.5 | " | " |
| 34 | " | " | " | " | " | K 0.07, Cu 0.1 | " | 690 |
| 35 | " | " | " | " | " | K 0.07, In 0.5 | " | " |
| 36 | " | " | " | " | " | K 0.07, Tl 0.03 | " | " |
| 37 | " | " | " | " | " | K 0.07, B 1.5 | " | " |
| 38 | " | " | 4.5 | 4.5 | " | K 0.07, Na 1.2 | " | 680 |
| 39 | " | " | " | " | " | K 0.07, Ag 1.2 | " | " |
| 40 | " | " | 3.7 | 6.8 | " | K 0.07, Sr 0.2 | " | " |
| 41 | " | " | 3.4 | 6.6 | " | K 0.07, Pb 0.4 | " | 690 |
| 42 | " | " | 2.7 | 6.6 | 0.3 | K 0.07, La 0.5 | " | 700 |
| 43 | " | " | " | " | " | K 0.07, Sm 0.5 | " | " |
| 44 | " | " | 3.6 | 6.0 | 1 | K 0.07, Mg 2 | " | 650 |
| 45 | " | " | " | " | " | K 0.07, Co 2 | " | " |
| 46* | — | " | 4.6 | 4.9 | " | K 0.3 | " | 690 |
| 47 | Pd 0.02 | " | " | " | " | " | " | " |
| 48 | Pd 0.05 | " | " | " | " | " | " | " |
| 49 | Pd 0.1 | " | " | " | " | " | " | " |
| 50 | Pt 0.04 | " | " | " | " | " | " | " |
| 51* | — | " | 3.1 | 4.5 | 0.3 | K 0.3 | " | 700 |
| 52 | Pd 0.05 | " | " | " | " | K 0.3, Ce 0.4 | " | " |
| 53* | — | " | 4.0 | 4.0 | 1 | K 0.3, Mn 2 | " | 680 |
| 54 | Pd 0.05 | " | " | " | " | K 0.3, Mn 2 | " | " |

Note
*A catalyst which falls outside the scope of the catalyst to be used in the process of the present invention.

EXAMPLE 1 AND COMPARATIVE EXAMPLE 1

Preparation of acrylonitrile

Ammoxidation reaction of propylene was carried out using Catalyst 6-A shown in Table 1.

In Table 1, Catalysts bearing an asterisk mark (*) are those falling outside the scope of the catalyst to be used in the process of the present invention and, hence, hereinafter often referred to as "Comparative" catalysts.

2 g of Catalyst 6-A was charged into a Vycor glass reaction tube having an inner diameter of 8 mm, and a gas mixture of propylene, ammonia, oxygen, steam and nitrogen was passed through the tube at a flow rate of 1.2 liters/hour (calculated in terms of NTP) at a temperature of 460° C. under atmospheric pressure. With respect to the composition of the gas mixture, the volume ratio of oxygen to propylene and that of steam to propylene were fixed at 1.9 and 1.0, respectively, while the volume ratio (R) of ammonia to propylene was varied within the range of 0.95 to 1.25 as indicated in Table 2 given below.

The concentration of propylene in the gas mixture was kept at 6% by volume by controlling the amount of nitrogen.

Further, using Comparative Catalyst 3 instead of Catalyst 6-A, the ammoxidation reaction was carried out in substantially the same manner as described above.

The products of these ammoxidation reactions were analyzed by gas chromatography, and the yield of acrylonitrile based on propylene (hereinafter often referred to as "$Y[C_3H_6]$") and the yield of acrylonitrile based on ammonia (hereinafter often referred to as "$Y[NH_3]$") were respectively determined according to the following formulae:

$$Y[C_3H_6] (\%) = \frac{\text{(Number of moles of acrylonitrile produced)}}{\text{(Number of moles of propylene fed)}} \times 100$$

$$Y[NH_3] (\%) = \frac{\text{(Number of moles of acrylonitrile produced)}}{\text{(Number of moles of ammonia fed)}} \times 100$$

In this connection, $Y[C_3H_6]$, $Y[NH_3]$ and R (the volume ratio of ammonia fed to propylene fed) satisfy the following relationship:

$$Y[NH_3] = Y[C_3H_6]/R$$

The results obtained are shown in Table 2.

TABLE 2

| | Catalyst 6-A | | Comparative Catalyst | |
|---|---|---|---|---|
| R | $Y[C_3H_6]$ | $Y[NH_3]$ | $Y[C_3H_6]$ | $Y[NH_3]$ |
| 0.95 | 83.5 | 87.9 | 78.6 | 82.7 |
| 1.00 | 84.4 | 84.4 | 80.4 | 80.4 |
| 1.05 | 85.2 | 81.1 | 82.0 | 78.1 |
| 1.10 | 85.6 | 77.8 | 83.3 | 75.7 |
| 1.15 | 86.1 | 74.9 | 84.4 | 73.4 |
| 1.25 | 86.5 | 69.2 | 85.6 | 68.5 |

It is apparent from the results shown in Table 2 that the smaller the value of R, the lower $Y[C_3H_6]$ but the higher $Y[NH_3]$.

FIGURE is a graph showing a relationship between $Y[C_3H_6]$ and $Y[NH_3]$, which is obtained based upon the data shown in Table 2. The graph given in FIGURE shows that when Catalyst 6-A is used, the yield of the resulting acrylonitrile based on ammonia is extremely high as compared with the case where Comparative Catalyst 3 is used. For example, as shown in the graph given in FIGURE, when the $Y[C_3H_6]$ value obtained by using Catalyst 6-A and that obtained by Comparative Catalyst 3 are both 84%, the $Y[NH_3]$ value obtained by using Catalyst 6-A is higher than that obtained by using Comparative Catalyst 3 by as much as 12%.

Using each of the catalysts 1 to 45 listed in Table 1, the ammoxidation reaction of propylene was carried out in substantially the same manner as described above. The reaction temperature and the flow rate of the gas mixture were varied according to the kind of the catalysts as shown in Table 3 below. The results are shown in Table 3.

TABLE 3

| | Catalyst | Reaction Temperature (°C.) | Flow Rate [liter (NTP)/hr] | R = 1.0 | | R = 1.15 | |
|---|---|---|---|---|---|---|---|
| | | | | $Y[C_3H_6]$ | $Y[NH_3]$ | $Y[C_3H_6]$ | $Y[NH_3]$ |
| Comparative | 1 | 450 | 1.8 | 73.8 | 73.8 | 76.5 | 66.5 |
| Present Invention | 2 | " | " | 81.9 | 81.9 | 82.8 | 72.0 |
| Comparative | 3 | 460 | 1.2 | 80.4 | 80.4 | 84.4 | 73.4 |
| Present Invention | 4 | " | " | 84.1 | 84.1 | 85.8 | 74.6 |
| Present Invention | 5 | " | " | 84.3 | 84.3 | 86.2 | 75.0 |
| Present Invention | 6-A | " | " | 84.4 | 84.4 | 86.1 | 74.9 |
| Present Invention | 6-B | " | " | 84.0 | 84.0 | 85.8 | 74.6 |
| Present Invention | 7 | 450 | 1.0 | 83.5 | 83.5 | 85.1 | 74.0 |
| Present Invention | 8 | 460 | 1.2 | 83.8 | 83.8 | 85.3 | 74.2 |
| Present Invention | 9 | 450 | 1.0 | 84.1 | 84.1 | 85.5 | 74.3 |
| Present Invention | 10 | 460 | 1.2 | 83.0 | 83.0 | 84.7 | 73.7 |
| Present Invention | 11 | " | " | 83.1 | 83.1 | 84.7 | 73.7 |
| Present Invention | 12 | " | " | 83.6 | 83.6 | 85.2 | 74.1 |

TABLE 3-continued

|  | Catalyst | Reaction Temperature (°C.) | Flow Rate [liter (NTP)/hr] | R = 1.0 | | R = 1.15 | |
| --- | --- | --- | --- | --- | --- | --- | --- |
|  |  |  |  | Y[C$_3$H$_6$] | Y[NH$_3$] | Y[C$_3$H$_6$] | Y[NH$_3$] |
| Present Invention | 13 | " | " | 83.2 | 83.2 | 84.8 | 73.7 |
| Present Invention | 14 | 450 | 1.0 | 83.8 | 83.8 | 85.3 | 74.2 |
| Comparative | 15 | 460 | 1.1 | 79.5 | 79.5 | 83.2 | 72.3 |
| Present Invention | 16 | " | " | 83.2 | 83.2 | 84.9 | 73.8 |
| Comparative | 17 | 460 | 2.2 | 82.1 | 82.1 | 87.5 | 76.1 |
| Present Invention | 18 | " | " | 84.8 | 84.8 | 87.9 | 76.4 |
| Comparative | 19 | 440 | 1.4 | 80.9 | 80.9 | 84.5 | 73.5 |
| Present Invention | 20 | " | " | 84.8 | 84.8 | 86.2 | 75.0 |
| Comparative | 21 | 460 | 1.2 | 80.3 | 80.3 | 84.5 | 73.5 |
| Present Invention | 22 | " | " | 84.5 | 84.5 | 86.3 | 75.0 |
| Present Invention | 23 | 460 | 1.2 | 84.3 | 84.3 | 86.2 | 75.0 |
| Present Invention | 24 | " | " | 84.2 | 84.2 | 85.9 | 74.7 |
| Present Invention | 25 | " | 1.0 | 83.1 | 83.1 | 84.5 | 73.5 |
| Present Invention | 26 | " | " | 82.6 | 82.6 | 84.0 | 73.0 |
| Present Invention | 27 | " | 1.2 | 83.5 | 83.5 | 85.1 | 74.0 |
| Present Invention | 28 | " | " | 84.0 | 84.0 | 85.8 | 74.6 |
| Present Invention | 29 | " | " | 83.4 | 83.4 | 84.9 | 73.8 |
| Present Invention | 30 | " | " | 83.7 | 83.7 | 85.6 | 74.4 |
| Present Invention | 31 | " | " | 83.3 | 83.3 | 84.8 | 73.7 |
| Present Invention | 32 | " | " | 83.1 | 83.1 | 84.6 | 73.6 |
| Present Invention | 33 | " | " | 83.3 | 83.3 | 85.0 | 73.9 |
| Present Invention | 34 | " | 1.0 | 83.0 | 83.0 | 84.8 | 73.7 |
| Present Invention | 35 | " | 1.2 | 83.8 | 83.8 | 85.2 | 74.1 |
| Present Invention | 36 | " | " | 84.1 | 84.1 | 85.8 | 74.6 |
| Present Invention | 37 | " | " | 83.5 | 83.5 | 84.1 | 73.1 |
| Present Invention | 38 | " | " | 83.6 | 83.6 | 85.4 | 74.3 |
| Present Invention | 39 | " | " | 83.8 | 83.8 | 85.3 | 74.2 |
| Present Invention | 40 | " | 1.5 | 83.6 | 83.6 | 85.1 | 74.0 |
| Present Invention | 41 | " | 1.1 | 83.2 | 83.2 | 85.0 | 73.9 |
| Present Invention | 42 | " | 2.2 | 84.2 | 84.2 | 87.5 | 76.1 |
| Present Invention | 43 | " | " | 84.0 | 84.0 | 85.8 | 74.6 |
| Present Invention | 44 | " | 1.2 | 82.8 | 82.8 | 84.7 | 73.7 |
| Present Invention | 45 | " | 1.4 | 83.0 | 83.0 | 84.8 | 73.7 |

As is apparent from Table 3, when the ammoxidation reaction of propylene was carried out using Comparative Catalyst 1 containing no ingredient A, the yield of acrylonitrile based on ammonia was low. On the other hand, when the ammoxidation of propylene was carried out using Catalyst 2 containing ingredient A, the yield of acrylonitrile based on ammonia was remarkably improved. Further, also in catalysts comprising molybdenum, bismuth, iron, phosphorus and other optional ingredients but containing no ingredient A, the incorporation of ingredient A to the catalysts provided an improved yield of acrylonitrile based on ammonia. This will be well understood if the data, as shown in Table 3, of Comparative Catalysts 3, 15, 17, 19 and 21 are compared with those of Catalysts 4 to 14, 16, 18, 20 and 22, respectively.

EXAMPLE 2 AND COMPARATIVE EXAMPLE 2

Preparation of methacrylonitrile

Using each of Catalyst 48 to be used in the process of the present invention and Comparative Catalyst 46 shown in Table 1, the ammoxidation reaction of isobutylene was carried out as follows.

1 g of Catalyst 48 was charged into a Vycor glass reaction tube having an inner diameter of 8 mm, and a gas mixture of isobutylene, ammonia, oxygen, steam and nitrogen was passed through the tube at a flow rate of 1.2 liters/hour (calculated in terms of NTP) at a temperature of 420° C. under atmospheric pressure. With respect to the composition of the gas mixture, the volume ratio of oxygen to isobutylene and that of steam to isobutylene were fixed at 2.5 and 1.0, respectively, while the volume ratio (R') of ammonia to isobutylene was varied within the range of 1.2 to 1.5 as shown in Table 4 below. The concentration of isobutylene in the gas mixture was kept at 6% by volume by controlling the amount of the diluent gas, nitrogen.

Using Comparative Catalyst 46 instead of Catalyst 48, the ammoxidion reaction was carried out in substantially the same manner as described above.

The products obtained by the above-mentioned reactions were analyzed by means of gas chromatography, and the yield of methacrylonitrile based on isobutylene ($Y[C_4H_8]$) and the yield of methacrylonitrile based on ammonia ($Y'[NH_3]$) were respectively determined according to the following formulae.

$$Y[C_4H_8]\ (\%) = \frac{\text{(Number of moles of methacrylonitrile produced)}}{\text{(Number of moles of isobutylene fed)}} \times 100$$

$$Y'[NH_3]\ (\%) = \frac{\text{(Number of moles of methacrylonitrile produced)}}{\text{Number of moles of ammonia fed}} \times 100$$

In this connection, $Y[C_4H_8]$, $Y'[NH_3]$ and R' (the volume ratio of ammonia fed to isobutylene fed) satisfy the following relationship:

$$Y'[NH_3] = Y[C_4H_8]/R'.$$

The results are shown in Table 4 below.

TABLE 4

| | Present Invention Catalyst 48 | | Comparative Catalyst 46 | |
|---|---|---|---|---|
| R' | $Y[C_4H_8]$ | $Y'[NH_3]$ | $Y[C_4H_8]$ | $Y'[NH_3]$ |
| 1.20 | 78.5 | 65.4 | 75.2 | 62.7 |
| 1.25 | 79.1 | 63.3 | 76.8 | 61.4 |
| 1.35 | 80.0 | 59.3 | 78.6 | 58.2 |
| 1.50 | 80.4 | 53.6 | 79.5 | 53.0 |

Using each of the catalysts 46 to 54 listed in Table 1, the ammoxidation of isobulylene was carried out in substantially the same manner as described above. The reaction temperature and the flow rate of the gas mixture were varied according to the kind of catalysts as shown in Table 5. The results are shown in Table 5.

TABLE 5

| | Catalyst | Reaction Temperature (°C.) | Flow Rate [liter (NTP)/hr] | R = 1.2 | | R = 1.35 | |
|---|---|---|---|---|---|---|---|
| | | | | $Y[C_4H_8]$ | $Y'[NH_3]$ | $Y[C_4H_8]$ | $Y'[NH_3]$ |
| Comparative | 46 | 420 | 1.2 | 75.2 | 62.7 | 78.6 | 58.2 |
| Present Invention | 47 | " | " | 77.2 | 64.3 | 79.3 | 58.7 |
| Present Invention | 48 | " | " | 78.5 | 65.4 | 80.0 | 59.3 |
| Present Invention | 49 | 410 | 1.0 | 78.1 | 65.1 | 79.8 | 59.1 |
| Present Invention | 50 | " | " | 77.8 | 64.8 | 79.6 | 59.0 |
| Comparative | 51 | 420 | 2.4 | 76.8 | 64.0 | 79.8 | 59.1 |
| Present Invention | 52 | " | " | 79.6 | 66.3 | 81.3 | 60.2 |
| Comparative | 53 | 420 | 1.2 | 75.6 | 63.0 | 78.8 | 58.4 |
| Present Invention | 54 | " | " | 78.7 | 65.6 | 80.5 | 59.6 |

What is claimed is:

1. A process for the preparation of acrylonitrile or methacrylonitrile comprising contacting at a temperature of 400° to 500° C. propylene or isobutylene with ammonia and molecular oxygen in the vapor phase in the presence of an oxide catalyst consisting essentially of 30 to 70% by weight of silica and supported thereon oxides of molybdenum, bismuth, iron and an ingredient A, said ingredient A being at least one element selected from the group consisting of palladium, platinum, osminum and iridium, the atomic ratio of molybdenum, bismuth, iron and the ingredient A being Mo:Bi:Fe:A = 12:0.5 to 10:0.5 to 10:0.002 to 0.2, said catalyst having been calcined at 600° to 710° C., no calination being effected at a temperature of higher than 710° C., before and after said calcination.

2. A process according to claim 1, wherein said ingredient A is present in an amount of 0.005 to 0.1 based on 12 atoms of molybdenum.

3. A process according to claim 1, wherein said ingredient A is palladium.

4. A process according to claim 2, wherein said ingredient A is palladium.

5. A process for the preparation of acrylonitrile or methacrylonitrile comprising contacting at a temperature of 400° to 500° C. propylene or isobutylene with ammonia and molecular oxygen in the vapor phase in the presence of an oxide catalyst consisting essentially of 30 to 70% by weight of silica and supported thereon oxides of molybdenum, bismuth, iron, an ingredient A and an ingredient X, said ingredient A being at least one element selected from the group consisting of palladium, platinum, osmium and iridium, said ingredient X being at least one member selected from the group consisting of alkali metals, alkaline earth metals, rare earth elements, tin, lead, titanium, zirconium, tungsten, vanadium, niobium, chromium, manganese, cobalt, nickel, zinc, copper, indium, thallium, boron and antimony, the atomic ratio of molybdenum, bismuth, iron, the ingredient A and the ingredient X being Mo:Bi:Fe:A:X=12:0.5 to 10:0.5 to 10:0.002 to 0.2:10 or less exclusive of zero, said catalyst having been calcined at 600° to 710° C., no calcination being effected at a temperature of higher than 710° C. before and after said calcination.

6. A process according to claim 5, wherein said ingredient A is present in an amount of 0.005 to 0.1 based on 12 atoms of molybdenum.

7. A process according to claim 5, wherein said ingredient A is palladium.

8. A process according to claim 6, wherein said ingredient A is palladium.

9. A process for the preparation of acrylonitrile or methacrylonitrile comprising contacting at a temperature of 400° to 500° C. propylene or isobutylene with ammonia and molecular oxygen in the vapor phase in the presence of an oxide catalyst consisting essentially of 30 to 70% by weight of silica and supported thereon oxides of molybdenum, bismuth, iron, an ingredient A and phosphorus, said ingredient A being at least one element selected from the group consisting of palladium, platinum, osmium and iridium, the atomic ratio of molybdenum, bismuth, iron, the ingredient A and phosphrous being Mo:Bi:Fe:A:P=12:0.5 to 10:0.5 to 10:0.002 to 0.2:0.1 to 3, said catalyst having been calcined at 600° to 710° C., no calcination being effected at a temperature of higher than 710° C. before and after said calcination.

10. A process according to claim 9, wherein said ingredient A is present in an amount of 0.005 to 0.1 based on 12 atoms of molybdenum.

11. A process according to claim 9, wherein said ingredient A is palladium.

12. A process according to claim 10, wherein said ingredient A is palladium.

13. A process for the preparation of acrylonitrile of methacrylonitrile comprising contacting at a temperature of 400° to 500° C. propylene or isobutylene with ammonia and molecular oxygen in the vapor phase in the presence of an oxide catalyst consisting essentially of 30 to 70% by weight if silica and supported thereon oxides of molybdenum, bismuth, iron, an ingredient A, an ingredient X and phosphorus, said ingredient A being at least one element selected from the group consisting of palladium, platinum, osmium and iridium, said ingredient X being at least one member selected from the group consisting of alkali metals, alkaline earth metals, rare earth elements, tin, lead, titanium, zirconium, tungsten, vanadium, niobium, chromium, manganese, cobalt, nickel, zinc, copper, indium, thallium, boron and antimony, the atomic ratio of molybdenum, bismuth, iron, the ingredient A, the ingredient X and phosphorus being Mo:Bi:Fe:A:X:P=12:0.5 to 10:0.5 to 10:0.02 to 0/2:10 or less exclusive of zero: 0.1 to 3, said catalyst having been calcined at 600° to 710° C., no calcination being effected at a temperature of higher than 710° C. before and after said calcination.

14. A process according to claim 13, wherein said ingredient A is present in an amount of 0.005 to 0.1 based on 12 atoms of molybdenum.

15. A process according to claim 13, wherein said ingredient A is palladium.

16. A process according to claim 14, wherein said ingredient A is palladium.

* * * * *